United States Patent
Voigt et al.

(10) Patent No.: US 9,245,091 B2
(45) Date of Patent: Jan. 26, 2016

(54) PHYSICALLY-CONSTRAINED MODELING OF A HEART IN MEDICAL IMAGING

(75) Inventors: Ingmar Voigt, Erlangen (DE); Razvan Ioan Ionasec, Lawrenceville, NJ (US); Bogdan Georgescu, Plainsboro, NJ (US); Tommaso Mansi, Westfield, NJ (US); Dorin Comaniciu, Princeton Junction, NJ (US); Helene C. Houle, San Jose, CA (US); Etienne Assoumou Mengue, Fürth (DE)

(73) Assignees: Siemens Aktiengesellschaft (DE); Siemens Corporation, Princeton, NJ (US); Siemens Medical Solutions USA, Inc., Malvern, PA (US)

( * ) Notice: Subject to any disclaimer, the term of this patent is extended or adjusted under 35 U.S.C. 154(b) by 929 days.

(21) Appl. No.: 13/416,216

(22) Filed: Mar. 9, 2012

(65) Prior Publication Data

US 2012/0232853 A1    Sep. 13, 2012

Related U.S. Application Data

(60) Provisional application No. 61/451,015, filed on Mar. 9, 2011.

(51) Int. Cl.
*G06F 19/00* (2011.01)
*G06T 7/00* (2006.01)

(52) U.S. Cl.
CPC .......... *G06F 19/3437* (2013.01); *G06F 19/321* (2013.01); *G06T 7/0032* (2013.01); *G06T 7/0089* (2013.01); *G06T 2207/20081* (2013.01); *G06T 2207/30048* (2013.01)

(58) Field of Classification Search
CPC . G06F 19/321; G06F 19/3437; G06T 7/0089; G06T 7/0032; G06T 2207/30048; G06T 2207/20081
See application file for complete search history.

(56) References Cited

U.S. PATENT DOCUMENTS

2010/0240996 A1    9/2010    Ionasec et al.

OTHER PUBLICATIONS

Armstrong, W. et al., "Feigenbaums Echocardiography." Lippincott Williams and Wilkins, pp. 32-41, 48-51, 160-161, 170-175, 214-231, and 234-245, 2009.
Borger, M. et al., "Chronic ischemic mitral regurgitation: Repair, replace or rethink?" Ann Thorac Surg (81), pp. 1153-1161, 2006.
Chung, E. S. et al., "Results of the predictors of response to crt (prospect) trial." Circulation (117), pp. 2608-2616, 2008.
Heimann, T. et al., "Statistical shape models for 3d medical image segmentation: A review." Medical Image Analysis 13(4), pp. 543-563, 2009.

(Continued)

*Primary Examiner* — Bo J Peng

(57) ABSTRACT

Physically-constrained modeling of a heart is provided. Patient-specific data may be used to estimate heart anatomy locations. A model is applied to the data for estimation. For increased accuracy of estimation, the biomechanics of the heart, such as the valve, may be used to constrain the estimation. By applying a dynamic system between estimated anatomy locations of different times, the locations may be deformed or refined. The modeled heart and/or valve may be used to estimate hemodynamics. The resulting velocities or other motion information may be used to emulate ultrasound Doppler imaging for comparing with acquired ultrasound Doppler data. The comparison may validate the modeling.

10 Claims, 8 Drawing Sheets

(56) References Cited

OTHER PUBLICATIONS

Hunter, P. et al., "A vision and strategy for the virtual physiological human in 2010 and beyond." Phil. Trans. R. Soc. A 368 (1920), pp. 2595-2614, Jun. 2010.

Ionasec, R. et al., "Patient-specific modeling and quantification of the aortic and mitral valves from 4D cardiac CT and TEE." IEEE Transactions on Medical Imaging, pp. 1636-1651, 2010.

Li, J. et al., "Numerical simulation of breakup of a viscous drop in simple shear flow through a volume-of-fluid method." Phys. Fluids 12 (2), pp. 269-282, 2000.

Mcqueen, D.M. et al., "A three-dimensional computer model of the human heart for studying cardiac fluid dynamics." SIGGRAPH 34 (1), pp. 56-60, Feb. 2000.

Mihalef, V. et al., "Atrioventricular blood flow simulation based on patient-specific data." Proceedings of FIMH, 2009.

Nesme, M. et al., "Efficient, physically plausible finite elements." Eurographics (short papers), pp. 77-80, 2005.

Papademetris, X. et al., "Estimation of 3D left ventricular deformation from echocardiography." Med Image Anal 5, pp. 17-28, Mar. 2001.

Quinones, M. A. et al., "Recommendations for quantification of Doppler echocardiography: A report from the Doppler quantification task force of the nomenclature and standards committee of the American society of echocardiography." J. Am. Soc. E (15), pp. 167-184, 2002.

Schenkel, T. et al., "Mri-based cfd analysis of flow in a human left ventricle: Methodology and application to a healthy heart." Annals of Biomedical Engineering (3), pp. 503-515, 2007.

Schievano, S. et al., "Percutaneous mitral valve dilatation: Single balloon versus double balloon." Journal of Heart Valve Disease 18 (1), pp. 28-34, 2009.

Schneider, R. et al., "Mitral annulus segmentation from 3D ultrasound using graph cuts." Medical Imaging, IEEE Transactions on 29 (9), pp. 1676-1687, 2010.

Sermesant, M. et al., "An electromechanical model of the heart for image analysis and simulation." IEEE Transactions in Medical Imaging 5 (25), pp. 612-625, 2006.

Votta, E. et al., "Mitral valve finite-element modelling from ultrasound data: a pilot study for a new approach to understand mitral function and clinical scenarios." Philosophical Transactions of the Royal Society A: Mathematical, Physical and Engineering Sciences 366 (1879), pp. 3411, 2008.

Wang, Y. et al., "Volumetric myocardial mechanics from 3D+t ultrasound data with multi-model tracking." Proceedings of STACOM, 2010.

Zheng, Y. et al., "Four-chamber heart modeling and automatic segmentation for 3-d cardiac ct volumes using marginal space learning and steerable features." IEEE Transactions on Medical Imaging 27 (11) pp. 1668-1681, 2008.

PHYSICALLY-CONSTRAINED MODELING OF A HEART IN MEDICAL IMAGING

RELATED APPLICATIONS

The present patent document claims the benefit of the filing dates under 35 U.S.C. §119(e) of Provisional U.S. Patent Application Ser. No. 61/451,015, filed Mar. 9, 2011, which is hereby incorporated by reference.

BACKGROUND

The present embodiments relate to modeling of the heart or components of the heart, such as the mitral valve. Medical imaging data is used to create patient-specific modeling.

Dysfunctional mitral valves (MV) are found in a large variety of cardiovascular diseases. Mitral valve prolapse for instance, where the leaflets billow into the left atrium due to dysfunctional chordae, is a common cause of regurgitation. A pathological left ventricular (LV) function, such as ischemic or idiopathic dilated cardiomyopathy, may yield severe mitral valve insufficiency due to an enlarged mitral annulus or abnormal positioning of the papillary muscles.

Echocardiography is used for MV assessment. The complex appearance of the MV, the fast dynamics, the large morphological and functional variations among patients, and the varying image quality (e.g., low signal-to-noise ratio, signal dropout, and/or time varying appearance) make the automatic modeling of the MV from echocardiography challenging.

Valve models may be generated manually or interactively. The process may be elaborate, tedious, and prone to inter-user variability. Even automatic modeling may have difficulties due to the echocardiography data. Temporal consistency and physiologically realistic deformations are not guaranteed. In contrast, deformable models integrating prior knowledge about the cardiac deformation may estimate the cardiac motion from images. However, their application for valve dynamics is challenged by the very rapid valve motion.

BRIEF SUMMARY

By way of introduction, the preferred embodiments described below include methods, computer readable media and systems for modeling of a heart. For physically-constrained modeling, patient-specific data may be used to estimate heart anatomy locations. A model is applied to the data for estimation. For increased accuracy of estimation, the biomechanics of the heart, such as the valve, may be used to constrain the estimation. By applying a dynamic system between estimated anatomy locations of different times, the locations may be deformed or refined.

The modeled heart and/or valve may be used to estimate hemodynamics. The resulting velocities or other motion information may be used to emulate ultrasound Doppler imaging for comparing with acquired ultrasound Doppler data. The comparison may validate the modeling. Other uses of the model than validation may be provided, such as for clinical or therapeutic uses.

In a first aspect, a method is provided for physically-constrained modeling of a heart. A processor estimates first anatomy locations of a valve of a patient from first medical diagnostic data of the patient at a first time. The processor estimates second anatomy locations of the valve of the patient from second medical diagnostic data of the patient at a second time different than the first time. The first anatomy locations for the first time are altered as a function of the second anatomy locations and a biomechanical model relating physical mechanics of the valve from the first and second times. The second anatomy locations for the second time are altered as a function of the first anatomy locations and the biomechanical model.

In a second aspect, a non-transitory computer readable storage medium has stored therein data representing instructions executable by a programmed processor for physically-constrained modeling of a heart. The storage medium includes instructions for determining first and second surfaces of a valve for first and second phases of a heart cycle. The determining is a function of first and second imaging data, respectively, input to a discriminative probabilistic model. Deformations of the first and second surfaces are calculated by solution of a dynamic system.

In a third aspect, a system is provided for physically-constrained modeling of a heart. An ultrasound scanner is configured to scan a heart volume of a patient. The scan provides medical diagnostic ultrasound data representing at least a part of the heart. A processor is configured to detect anatomical components of at least the part of heart from the medical diagnostic ultrasound data. The detection is based, at least in part, on a constraint from a biomechanical property of the heart. The processor is configured to generate a representation of the at least part of the heart. A display is configured to generate a visualization of the representation.

In a fourth aspect, a non-transitory computer readable storage medium has stored therein data representing instructions executable by a programmed processor for computation of fluid-dynamics based patient-specific heart anatomy and dynamics. The storage medium includes instructions for modeling components of the heart, calculating hemodynamics of the heart from the modeling, and emulating Doppler flow values for different locations from the hemodynamics.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Some embodiments below relate to robust physically-constrained modeling of the heart, such as the mitral valve and subvalvular apparatus. Other embodiments relate to use of this modeling and/or other modeling of the heart. These other embodiments provide for validation of patient-specific modeling using hemodynamics.

Physically-constrained modeling may be used for the mitral valve (MV). Due to the complex shape and dynamics of the MV, patient-specific modeling of the MV constitutes a particular challenge. Personalized modeling of the dynamic MV and the corresponding subvalvular apparatus may ensure temporal consistency over the cardiac sequence and provide realistic deformations. The anatomical MV components are detected under constraints derived from the biomechanical properties of the leaflets. The model is automatically initialized in the images, and local minima are avoided through incremental search and discriminative learning. A robust two-step alternating algorithm combines discriminative learning and leaflet biomechanics. The biomechanical constraint is ensured by solving a dynamic system between time frames.

The model includes the MV annulus, anterior and posterior leaflets, and the subvalvular apparatus represented by landmarks at the papillary tips. The model may be used to detect and/or quantify remodeling of annulus and leaflets in functional mitral regurgitation.

Another use of this model or a different model may be for validation. The model is validated prior to release for clinical or therapeutic use. Patient-specific models of the heart physiology may improve the diagnosis and treatment of cardiac disease. The model may represent the complex functional and hemodynamic interdependencies among the anatomical structures. For example, the left-side heart is modeled based on data of the morphology, function, and hemodynamics.

For validation, patient-specific fluid dynamics are computed over the cardiac cycle using embedded boundary and ghost fluid methods, constrained by the dynamics of the anatomical model. The hemodynamics are used to emulate ultrasound Doppler data. Qualitative and quantitative validation of the computed blood dynamics is performed against actual Doppler echocardiography measurements.

Figure 1:
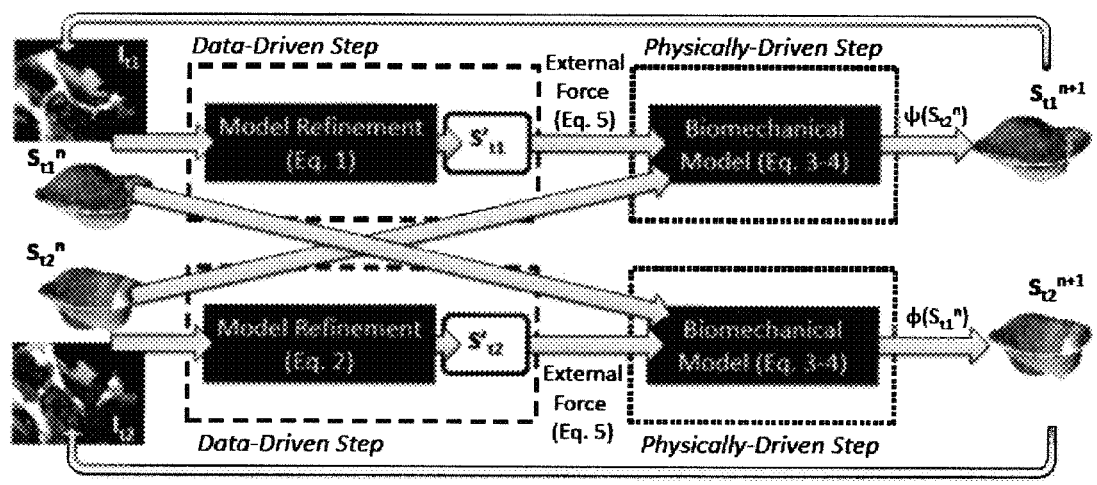
FIG. 1 is an example illustration of a framework for physically-constrained modeling of a heart.

FIG. 1 shows a framework for physically-constrained valve estimation. A physiologically realistic four dimensional (i.e., three spatial dimensions (3D) over time (t)) model of the MV and the corresponding subvalvular apparatus is created. The model may be estimated from 4D (i.e., 3D+t) cardiac images. A machine learning or other modeling approach is constrained such that the estimated point distribution model $S \in \Omega$, $\Omega$ being the space of physiological surface shapes, satisfies MV biomechanics. The constrained problem may be written as:

$$S_{t1} = \arg\max \rho(\hat{S}|I_{t1}) \text{ for } \hat{S} \in \Omega \quad (1)$$

$$S_{t2} = \arg\max \rho(\hat{S}|I_{t2}) \text{ for } \hat{S} \in \Omega \quad (2)$$

$$S_{t2} = \phi(S_{t1}) \text{ and } S_{t1} = \psi(S_{t2}) \quad (3,4)$$

where $\rho$ is a discriminative probabilistic model and $\phi$ and $\psi$ are the physiological deformations calculated by solving a dynamic system.

To achieve computational efficiency, this high-dimensional constrained and coupled problem is solved with a two-step optimization procedure, as illustrated in FIG. 1. At a given iteration n of the processing loop, $S_{t1}{}^n$ and $S_{t2}{}^n$ are the current physically constrained models in images, $I_{t1}$ and $I_{t2}$, respectively. In the first data-driven step, $S_{t1}{}^n$ is refined using discriminative machine learning or other anatomical modeling on $I_{t1}$ to obtain a new estimate $S_{t1}'$ (Eq. 1). In the second physically-driven step, $S_{t2}{}^n$ is deformed according to the biomechanical model $\psi$ with external force calculated from $S_{t1}'$ to obtain an updated physically constrained $S_{t1}{}^{n+1}$ (Eq. 3). The updated model in image $I_{t1}$ is a deformed realization of $S_{t2}{}^n$ from image $I_{t2}$ subject to data-driven information related to $I_{t1}$. $S_{t2}{}^{n+1}$ is computed in parallel following the same procedure for equations 2 and 4.

Figure 2:
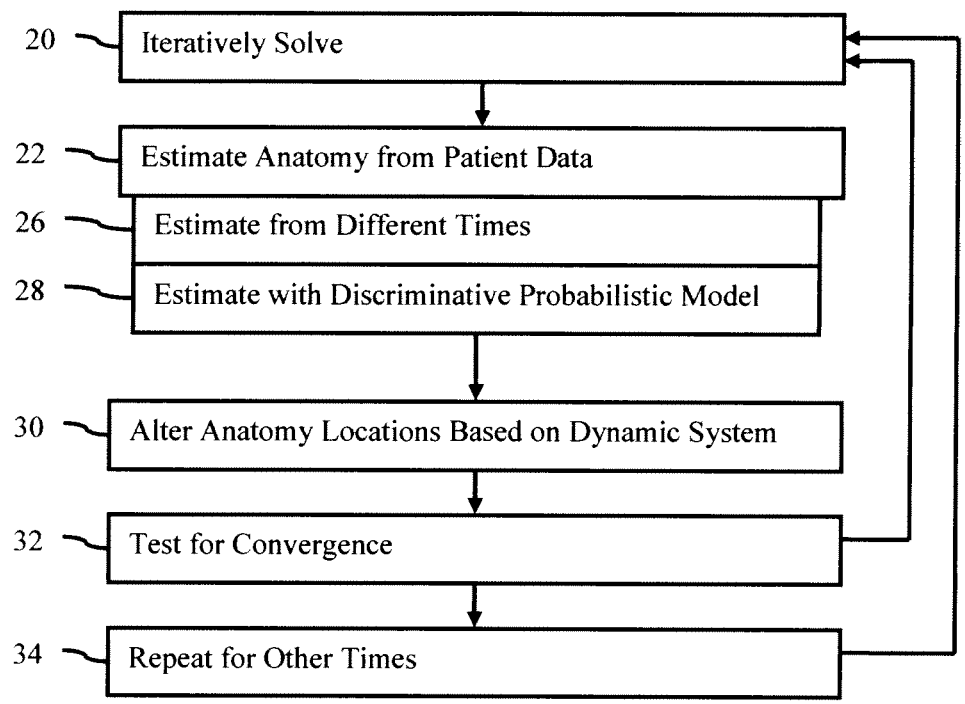
FIG. 2 is a flow chart diagram of one embodiment of a method for physically-constrained modeling of a heart.
Figure 10:
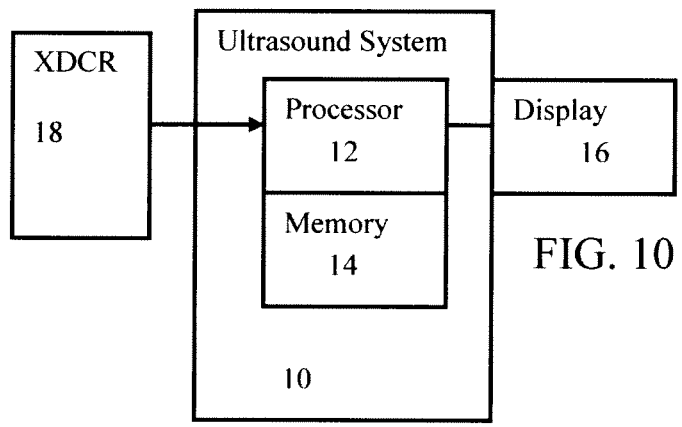
FIG. 10 is a block diagram of one embodiment of a system for physically-constrained modeling of a heart and/or validation of modeling.

FIG. 2 shows a method for physically-constrained modeling of a heart. The method is implemented by a medical diagnostic imaging system, a review station, a workstation, a computer, a PACS station, a server, combinations thereof, or other device for image processing medical diagnostic data. For example, the system or computer readable media shown in FIG. 9 implements the method, but other systems may be used.

The method is implemented in the order shown or a different order. Additional, different, or fewer acts may be performed. For example, the process is performed once for a given pair of images or frames of data, so acts 20, 32, and/or 34 are not performed. Acts 22 and 30 may be performed without other acts.

The acts are performed in real-time, such as during scanning. The model may be created while scanning to acquire another dataset representing the volume. The acts may be performed during an appointment or off-line in a review period. The patient-specific data may be associated with previous acquisition rather than in real-time. Measurements and/or images of automatically detected anatomy may be provided in seconds, such as 10 or fewer seconds. Alternatively, the acts are performed as desired by a surgeon regardless of whether a patient is currently at the facility or being scanned.

The acts may be performed automatically by a processor. The user causes the patient to be scanned or obtains scan data for the patient from a previous scan. The user may activate the process. Once activated, the anatomy is identified and refined through a sequence of images or scan data for estimating the anatomy model in act 22 and altering the anatomy locations in act 30 without further user input. User input of locations of the anatomy in any of the scan data may be avoided. Some user input may be provided, such as for changing modeling parameter values, correcting detected locations, and/or to confirm accuracy.

The model is based on scan data from a patient. This patient-specific modeling may result in the anatomy locations being different for different patients. For one patient, the relative locations of valve anatomy for a given time and/or the change in position over time may be different than for another patient. Patient-specific data is used to create the model.

The modeling and patient-specific fitting of the model may be performed for any valve or heart valve. In one embodiment, a single heart valve is identified and parameterized. In other embodiments, more than one heart valve is identified and parameterized at a same time or during a same imaging session. For example, the mitral valve and the aortic valve are physiologically modeled. The whole heart, half the heart, or other sub-portion of the heart may be modeled.

For patient specific modeling, one or more sets of data are obtained. Ultrasound or computed tomography data is obtained. Any medical imaging modality capable of scanning a volume multiple times during a heart cycle may be used, such as TEE echocardiography. The ultrasound data corresponds to a data set interpolated to a regular 3D grid, displayed images (e.g., detected and scan converted ultrasound data), beamformed data, detected data, and/or scan converted data. Imaging data may be a frame or volume of data representing a volume. The imaging data may be data from the processing path derived before generating an image or data for a display as an image. A frame or volume of data may be data in an image format or data in a different format (e.g., scan format or representing a three-dimensional grid). The ultrasound data represents a volume or 3D region of a patient.

The volume region includes tissue, fluid, or other structures. Different structures or types of structures react to the acoustic energy differently. The shape of a structure or spatial aspect may be reflected in B-mode or harmonic data. The flow of fluid may be reflected in color flow, Doppler, spectral Doppler, or Doppler flow data.

In act 20, the estimation and alteration acts 22 and 30 are configured to be solved iteratively. For a given pair of frames, the estimation of the model as constrained by the biomechanical operation is performed multiple times until the solution sufficiently converges. In alternative embodiments, the estimation and alteration are performed once for a given pair of frames of data.

The method may be performed for two frames representing different times. The heart cycle is cyclical, so has phases. Example phases are diastole and systole. The method is performed on two frames of data from different times and representing different phases of the heart cycle. For example, one frame represents diastole and the other frame represents the heart volume 0.05-0.3 seconds later.

The method may be applied on the entire 4D time series of frames, such as performing the method for a moving window of pairs of frames throughout the cycle. Any number of frames for a given cycle and corresponding phases may be used, such as 2-40. The frames representing different phases may be acquired from different cycles, but are temporally positioned to represent the heart over a cycle. The description below is for two frames $I_{t1}$ and $I_{t2}$ at times t1 and t2 only, for the sake of clarity.

In act 22, the locations of anatomy are estimated. For patient-specific estimation, the locations of the anatomy are estimated using medical diagnostic data of the patient. Data representing the valve or volume of the heart is used for determining the locations of the anatomy.

The estimation is performed for each of the frames of data or different times as represented by act 26. The estimation for the different frames may initially be independent of estimation for other frames. For later iterations, the estimation for any given frame may be based, at least in part, on the estimated locations of the anatomy in frames representing other phases. Since each frame is for a different phase, the estimates are of the locations of the anatomy at different times.

Figure 3:
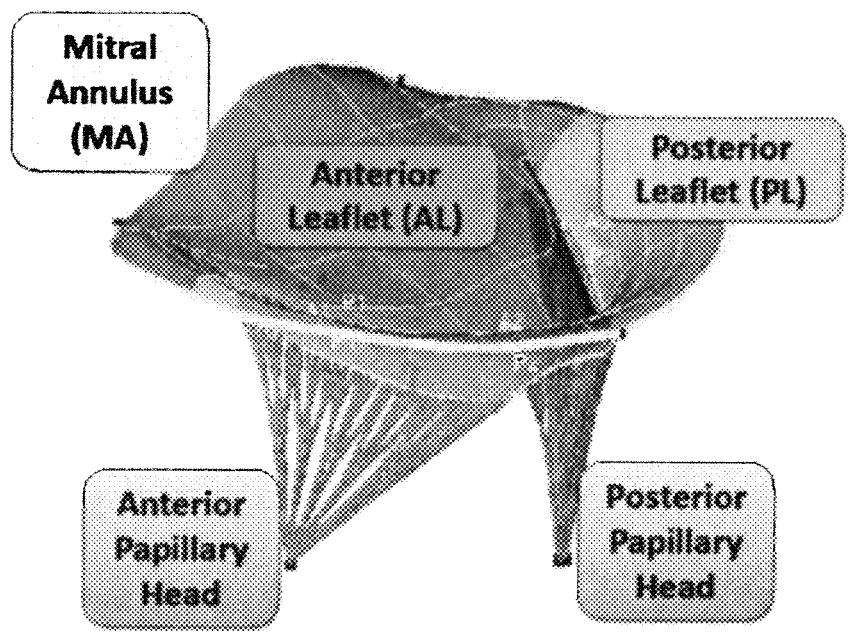
FIG. 3 is an illustration of example landmarks and mesh for a heart valve.

The processor estimates an anatomy model of the valve of a patient from the medical diagnostic imaging data of the patient. The model represents relative locations of anterior papillary head, posterior papillary head, mitral annulus, anterior leaflet (AL) and posterior leaflet (PL). FIG. 3 shows these locations on a representation of the mitral valve at systole. The papillary heads are for chordae. Additional, different, or fewer anatomic locations may be used, such as the papillary tips. The same or different model is used for detecting the anatomy at different phases.

The estimation is data-driven. For determining the location, shape, motion, size or other characteristic of a heart valve, the valve is modeled generally. The model is fit to patient specific data by estimation. Any estimation may be used, such as disclosed in U.S. Published Patent Application No. 2010/0240996, the disclosure of which is incorporated by reference. The estimation is performed in sequential stages, such as associated with a hierarchal model. For example, a location of the global valve relative to the heart volume is estimated, one or more locations in the valve relative to other portions of the valve are then estimated, and then a surface of the valve is estimated. Each stage may use the same or different algorithms. For example, separate machine-learnt algorithms are used for each stage. Different models may be estimated from the frames of data for different stage, phase, or type of anatomy.

In one embodiment, a physiological model of the aortic and mitral valves is designed to capture complex morphological, dynamical and pathological variations. The hierarchical definition is constructed on three abstraction levels: global location and rigid motion model, non-rigid landmark motion model, and comprehensive aortic-mitral model. Along with the parameterization, an anatomically driven re-sampling method to establish point correspondence required for the construction of a statistical shape model is provided. A collision detection and repair algorithm may provide physiological consistency.

For estimating from the model relative to a particular patient, patient-specific aortic-mitral model estimation is provided. The model parameters are estimated from volumetric sequences (3D+time data) to construct patient-specific aortic-mitral representations. The estimation is from ultrasound, CT, or other data representing a volume including the valve over time. For example, MV anatomy is estimated from 3D+t TEE images.

To capture a broad spectrum of morphological variations, the model is parameterized by three coarse-to-fine components: i) three transformations B for global location, orientation and scale over the cardiac cycle; ii) the trajectories of ten anatomical landmarks $L(B)=(l1 \ldots l10) \in R^{3 \times 10}$ (e.g., two trigones, one posterior annulus mid-point, two commissures, two leaflet tips and three papillary tips); and iii) a triangulated surface mesh $S_{LA}(B, L)$ to represent the left atrial (LA) surface of both anterior and posterior leaflets. The positions of the vertices of the LA surface are constrained by the anatomical landmarks, resulting in an anatomically consistent parameterization that ensures intra- and inter-patient point correspondence.

Other meshes may be used, such as tetrahedral mesh. The estimated mesh represents the valve. The mesh represents a surface of the valve. Different surfaces, S, are determined for the different times or phases of the heart cycle. In one embodiment, the surfaces, S, are each a point distribution model of 986 points and 1792 triangles with consistent parameterization derived from anatomical landmarks (three trigones, three commissures, two leaflet tips and three papillary heads). Other numbers of vertices and/or triangles may be used.

Any model may be used. In one embodiment represented by act 28, the estimation is a function of a discriminative probabilistic model, such as represented in equations 1 and 2. The model detects the locations of anatomy based on probability. The location associated with a highest probability, after any weighting or other consideration, is selected as the location for the anatomy. Different locations have different probabilities for representing the anatomy of interest. One type of discriminative probabilistic model is a machine-learned model. Other models may be used.

Combinations of different types of models may be used for the anatomy model. For example, different detectors are employed for the mitral annulus and free-edges contours and the leaflet surfaces to improve detection accuracy.

The anatomy model is estimated from the patient specific data. The patient specific data is an input feature to the model, such as a machine-learned matrix. In one embodiment, B, L(B) and $S_{LA}$(L, B) are estimated from the frames of data using a hierarchical discriminative learning algorithm. The probability p(B, L, S|I), given the frame of data I, is incrementally modeled within the Marginal Space Learning (MSL) framework, based on the Probabilistic Boosting Tree (PBT). Given a test image, the MLS framework finds position candidates around the MV based on Haar and/or steerable features. The position candidates are then successively refined by rotation and scaling candidates. This defines a region of interest inside which the positions of ten landmarks are estimated using the same strategy.

In one embodiment, a robust learning-based algorithm, which in concordance with the hierarchical parameterization, includes three stages: global location and rigid motion estimation, non-rigid landmark motion estimation and comprehensive aortic-mitral estimation. Each stage may be implemented differently. In one embodiment, trajectory spectrum learning (TSL) with local-spatio-temporal (LST) features is used for the non-rigid landmark motion estimate. The number of stages may be fewer or more. The same algorithm is used for either ultrasound or computer tomography data. Alternatively, different algorithms are trained for the different types of data.

Any machine training may be used for one or more stages. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used.

The classifier is trained from a training data set using a computer. Any number of expert annotated sets of data is used. For example, about 200 hundred volume sequences representing the heart and including one or more valves are annotated. The annotation indicates valve landmarks and/or surfaces within the volumes. The different anatomies of each volume are annotated. This large number of annotations allows use of a probabilistic boosting tree to learn relevant features over a large pool of 3-D Haar, and/or steerable features. Both features may be efficiently computed and be effective as a feature space for boosting classifiers. Other features may be used. Each classifier uses the data sets and annotations specific to the anatomy being classified.

In one embodiment, the classifier is a knowledge-based probabilistic model, such as marginal space learning using a hierarchical search. A database of known cases is collected for machine learning, providing a database-driven knowledge-based approach. For training data, three-dimensional context information is preserved and guides the detection process. Training and detecting the location of measurement indicators include detecting the associated anatomy since the measurement indicator indicates the anatomy. The classifier learns various feature vectors for distinguishing between a desired anatomy and information not being detected. In alternative embodiments, the classifier is manually programmed.

For learning-based approaches, the classifier is taught to distinguish based on features. For example, the probability model algorithm selectively combines features into a strong committee of weak learners based on Haar-like local rectangle filters whose rapid computation is enabled by the use of an integral image. Features that are relevant to the anatomies are extracted and learned in a machine algorithm based on the experts' annotations, resulting in a probabilistic model. A large pool of features may be extracted. The training determines the most determinative features for a given classification and discards non-determinative features. Different combinations of features may be used for detecting different anatomies, the same anatomy at different resolutions, and/or the same anatomy associated with different translation, rotation, or scale. For example, different sequential classification stages utilize different features computed from the 3D volume data. Each classifier selects a set of discriminative features that are used to distinguish the positive target from negatives. The features are selected from a large pool of features. The large pool is determined by a programmer or may include features systematically determined.

A tree structure may be learned and may offer efficiency in both training and application. In the midst of boosting a multi-class classifier, one class (or several classes) may have been completely separated from the remaining ones and further boosting yields no additional improvement in terms of the classification accuracy. For efficient training, a tree structure is trained. To take advantage of this fact, a tree structure is trained by focusing on the remaining classes to improve learning efficiency. Posterior probabilities or known distributions may be computed, such as by correlating anterior probabilities together.

To handle the background classes with many examples, a cascade training procedure may be used. A cascade of boosted binary-class strong classifiers may result. The cascade of classifiers provides a unified algorithm able to detect and classify multiple objects while rejecting the background classes. The cascade structure corresponds to a degenerate decision tree. Such a scenario presents an unbalanced nature of data samples. The background class has voluminous samples because all data points not belonging to the object classes belong to the background class. Alternatively, the classifiers are sequentially trained without cascade.

The probabilistic boosting tree (PBT) unifies classification, recognition, and clustering into one treatment. A probabilistic boosting tree is learned for each anatomy or stage of interest. The classifier is a tree-based structure with which the posterior probabilities of the presence of the anatomy of interest are calculated from given data. Each detector not only provides a binary decision for a given sample, but also a confidence value associated with the decision. The nodes in the tree are constructed by a combination of simple classifiers using boosting techniques.

By inputting the patient-specific data, the anatomy model is estimated for a given patient. The locations for the anatomy are estimated for a given time, such as end-diastole, and/or for a sequence of times, such as throughout a heart cycle. The anatomy model may include input information not obtained from the scan data.

The anatomy model may include a mesh fit to the valve based on the detected anatomy (see FIG. 3). The model outputs the mesh or the mesh is formed based on the locations of anatomy output by the model. The point-distribution model of the MV surface is mapped according to the landmarks and deformed, within the learned space of shapes, according to boundary detectors estimated through PBT.

The MV anatomy is tracked over the cardiac sequence using a manifold-based motion model. Alternatively, independent detection is used for other phases.

The same or different model or group of models is used for the initial identification of anatomy locations. For example, the locations are detected in a first iteration or in preparation for a first iteration. For later iterations, the locations (e.g., surface, area, line, or point) are refined. The model may accept as input the frame of scan data and/or the surface. In one embodiment, the surface position is refined by using a previously detected surface and the patient-specific data as inputs to the model. The refining uses a machine-learned matrix of a discriminative probabilistic model. The initial detection uses the same or different machine-learned matrix.

In act 30, the locations detected by the anatomy model for a given iteration are altered. The locations, such as specific points, lines, areas, volumes, or surfaces, of anatomy are changed. The alteration may or may not occur. For example, part of a surface, such as associated with the leaflets, is translated and/or rotated. Another portion of the surface, such as associated with the mitral annulus, remains the same. All portions may remain the same or change. Some portions may change and others not.

The alteration is of the anatomy locations for a given phase or time. The anatomy locations for each of the times are altered independently. Alternatively, the anatomy locations for one time are altered, at least in part, based on alteration of anatomy locations for another time. For example, the anatomy locations for a first phase (e.g., diastole) are altered in one iteration. For a subsequent iteration, these altered locations or the alteration itself (e.g., magnitude and/or direction of change) may be used in determining the alteration of the locations in a second phase (e.g., diastole +/− one phase increment). The alteration for one time may or may not be used for alteration of a different time in the same iteration.

In one embodiment, the alteration of anatomy locations for a given time is a function of anatomy locations of a different time and a biomechanical model. The anatomy locations from a different time are used as a starting point for the biomechanical model. The biomechanical model relates the physical mechanics of the valve from one time to another time. Based on the physics or physical structure, the biomechanical model is applied to determine the change in the anatomical locations over time to the given time.

For a pair of frames, a converse alteration is performed. For time one, the locations from time two are used as the starting point for the biomechanical transform to time one. For time two, the locations from time one are used as the starting point for the biomechanical transform to time two.

The deformations between times are calculated by solution of a dynamic system. The dynamic system represents the change due to physical operation of the valve. For example, the dynamic system includes terms for mass, damping, stiffness, displacement, velocity, and acceleration. Additional, different, or fewer terms may be used to represent the operation of the valve.

The biomechanical model is applied in the alteration as a physically driven step. The biomechanical model is a constraint on the detection of anatomy locations by the anatomy model. By using the altered anatomy locations from a different phase as an input to the anatomy model, the detected anatomy locations are influenced by the altered anatomy locations.

In one embodiment, the alteration is performed by weighting the application of the probabilities in the anatomy model. The estimations in $I_{t1}$ and $I_{t2}$ are constrained according to the biomechanical model of the MV leaflets. $S_{t1}''$ and $S_{t2}''$ are the current physically-constrained model, and $S_{t1}'$ and $S_{t2}'$ are the new estimates. The updated constrained model $S_{t1}''^{n+1}$ related to $I_{t1}$ is obtained by deforming $S_{t2}''$ towards $S_{t1}'$. This deformation, $\psi$ in equation 3, is achieved by solving the dynamic system $$M\ddot{U}+C\dot{U}+KU=F_{ext} \quad (5)$$

where U is the displacement vector of the vertices of $S_{t2}''$, $\dot{U}$ is the velocity of the vertices, and $\ddot{U}$ is the acceleration of the vertices, M is a diagonal mass matrix (e.g., leaflet mass density $\rho=1.04$ g/mL), C is a Rayleigh damping matrix (e.g., C=0.1(M+K), and K is the stiffness matrix of the internal elastic forces. The tissue properties of the leaflets are represented as a linear isotropic material to optimize computational efficiency for fast estimation. The leaflet thickness is set to 2 mm since imaging may not accurately represent this thickness. The thickness is an average from representative patients, but other thicknesses may be used. Near-incompressibility is achieved with a Poisson ratio v of 0.488 and a Young modulus E of 6.2 MPa. Other dynamic representations of the biomechanical model may be used.

The leaflets are modeled as linear, transverse isotropic elastic tissues. The leaflets may behave as linear materials in the range of physiological pressures even if modeled throughout the cycle. Linear elasticity models are also computationally efficient, allowing fast simulations and real-time intervention planning. Any linear relationship may be used for basal and marginal regions, such as an initial generally inelastic region followed by a linear increase in elasticity as a function of force. In alternative embodiments, the curved lines or other representation of the leaflet tissue is used.

Different or the same tissue properties are assigned to the AL and PL, such as AL Young's modulus of $E_{ALf}=6.233$ MPa, $E_{ALf\perp}=2.350$ MPa, AL shear modulus of $G_{f\!f\!\perp}=1.369$ MPa, PL Young's modulus of $E_{PLf}=2.087$ MPa, $E_{PLf\perp}=1.887$ MPa, and PL shear modulus of $G_{f\!f\!\perp}=0.694$ MPa. Other values representing the tissue may be used.

In the dynamic system, the force applied for solving the biomechanical model emulates a spring. Other forces may be added or used instead of a spring force.

The force is directional, such as at a normal to the anatomical location. The normal is at the surface for each location, such as at each vertex. Force at other directions may be used.

The force may be weighted. For example, the force is weighted by an amount of altering. Greater alterations may result in greater force. A difference in velocity, position, or acceleration of vertices from different times is used as the weight. The inverse relationship may be used. Other or no weighting may be used.

The force is calculated from the surface or other anatomy locations at one time for alteration of the anatomy locations for a different time. The surface for the one time is deformed based on the biomechanical model of the valve with the external force calculated from the surface used as the starting point for application of the force.

In one embodiment, $F_{ext}$ is the external force that drives $S_{t2}''$ towards the new estimate $S_{t1}'$. To make the result as close as possible to $S_{t1}'$ while preserving the tangential motion generated by the internal forces, the vertices $v_{t2}''$ of $S_{t2}''$ are moved long their normal direction n, towards their corresponding vertex $v_{t1}'$ in $S_{t1}'$. The force is weighted according to the uncertainty in the data term $\rho(v_{t1}'|I_{t1})$ such that positions with low confidences have little influence on the leaflet deformation, while high confidences result in high influence. For example, $F_{ext}$ is written as:

$$F_{ext}(v_{t2}'')=-\kappa\rho(v_{t1}'|I_{t1})(v_{t1}'-v_{t2}'')\cdot n \quad (5)$$

where $\kappa$ is a weight parameter. Any value may be used, such as empirically setting $\kappa$ to 0.1.

The alteration is performed with the biomechanical model as a finite element model. The various components are spatially and temporally handled in discrete steps. The dynamics are solved as a linear system using acceleration, velocity and position.

In one embodiment, the vertices $v_{t2}{}''$, and thus the force $F_{ext}$, are updated at every time step of the resolution of the dynamic system in equation 5. The equation is solved using co-rotational triangular finite element methods (FEM) to cope with large deformations and rotations of the anatomy of the valve. An implicit Euler solver is employed to update mesh positions. The deformation ends when the average relative displacement of the surface vertices is lower than the image resolution (typically 1 mm). This solution is performed for the altering of each iteration. The dynamic system is solved for a given alteration.

The finite element modeling is performed without user input of anatomy locations. The user may activate the creation of models and simulation, but input of locations of anatomy is avoided. The simulation is performed automatically. In alternative embodiments, the user confirms or indicates locations of anatomy for creation of models or control of the closure simulation.

In act 32, the valve model is tested for convergence. After performing the estimation and the alteration, the model is tested. To test a given iteration for convergence, the difference between the altered anatomical locations and estimated anatomical locations is determined. Any difference measure between points in a volume and/or surfaces may be used, such as a minimum sum of absolute differences. In one example, a maximum (e.g., Hausdorff) difference is used. An average (mesh-to-mesh) distance in mm may be used.

The anatomical model and alteration from the anatomical model are iterated until convergence. The final deformed model $\psi(S_{t2}{}'')=S_{t1}{}^{n+1}$ matches the estimated model $S_{t1}{}'$. The new model $S_{t1}{}^{n+1}$ takes into account the internal forces and is robust to outliers with low confidence from the data term (e.g., the probability or estimation from patient-specific data). The new model is also physically consistent with $S_{t2}{}''$. The same test is symmetrically applied for the estimate $S_{t2}{}^{n+1}$.

Convergence is found when the similarity is sufficient, such as representing a threshold difference or less. For example, convergence occurs when the average or other difference between two surfaces is at or below the resolution of the ultrasound data. Alternatively, convergence is found when a local or global minima is reached. Other tests for convergence may be used. As the model comes closer to the maximum PBT, an equilibrium is found.

If the surfaces from the alteration act 30 and the anatomy estimation act 22 are not converged, the acts 22 and 30 are repeated. This repetition is represented by the feedback in FIG. 2 from act 32 to act 20.

In act 34, the process of acts 20-32 is repeated for other pairs of frames. The estimating, altering and repeating of the estimating and altering until convergence are performed for data from a different phase of the heart cycle. Alternatively, the method is not repeated. A moving window may be used, such that the model for one phase is processed with the prior and subsequent phase.

The repetition extends the model to the 4D sequence. The models are propagated over the cardiac sequence using a cyclic constraint and iterating until convergence. The process ends when the norm of the maximum update displacement in all the frames is below the image resolution or other measure of convergence.

The surface or other anatomy locations are used for analysis and/or imaging. For example, a value representing operation or other characteristic of the valve is calculated from the surface at a given time or from surfaces from different phases.

For imaging, an image of the valve is generated. The image is from the acquired scan data and/or from the model. For example, the mesh representing the valve may be used for imaging. The image is a rendering of a three-dimensional volume. Voxels or data representing three-dimensional locations are rendered to a two-dimensional view. Ray casting, projection, surface or other rendering may be used.

In one embodiment, the surface is overlaid on a rendering of the heart or valves. The valve images are rendered from medical data with a same scale and perspective as an outline overlaid on the rendering. Color coding or other display modulation may be used with or in addition to an overlay. For example, different surfaces of the valve are rendered from B-mode data in gray scale with color modulation specific to the simulated surface. One surface may be rendered in one color and another in another color.

One rendering or multiple renderings from the same volume may be displayed. In one embodiment, a sequence of images is displayed. The sequence is rendered from the different volumes throughout a portion (e.g., simulating closure) of or the entire heart cycle. For each image in the sequence, the corresponding detected or estimated valve information is displayed. The surface corresponding to the valve at the given time represented by an image is displayed. The images of the sequence may be displayed in succession to show or represent the motion of the valve. The representation of the valve is generated as a function of the surfaces simulated through the sequence.

In one example, 200 4D TEE studies from 120 patients are acquired using different capture ranges and image resolutions. Each study is associated with ground-truth models, which are manually fitted to the image data. The performance results are obtained using three-fold cross validation experiments for both biomechanically constrained and unconstrained estimation schemes. The same anatomy model is used for both approaches.

The method performs with a speed of 9 seconds per volume on a standard desktop machine (Intel Core Duo 2.66 GHz, 2 GB RAM). The biomechanical deformations may use 5 to 25 iterations to converge. The overall algorithm may converge in 5 to 7 iterations without convergence problems. Other speeds and/or numbers of iterations may be provided.

The average point-to-mesh accuracy relative to a ground truth may be comparable for both constrained and unconstrained methods. Considering the 1 mm image resolution, the Haussdorff distances may underline the specific strength of the biomechanical constraint by providing improved robustness over the purely data driven approach especially in cases with challenging image quality. Use of the biomechanical constraint may constitute an improvement of up to 11.5%, while at the same time preserving a reasonable estimation speed of 9 seconds per volume. The average Hausdorff error may be about 5.1 mm.

The leaflets and free edges of the valve, which are governed by rapid motion and signal dropout, especially in diastole, may benefit from the constrained estimation scheme. For example, the unconstrained estimation algorithm may fail to delineate the mitral valve due to image noise, while the biomechanical constraint compensates for such outliers and provides realistic shapes and smooth surfaces. Using the biomechanical model of the valves, temporal consistency and physiological variation in anatomical dimensions reflects the near-incompressibility of the tissue. The relative temporal variation in surface area and leaflet length may be consistently lower using the biomechanical constraint and quantifies to 10% verses 14% for the constrained verses unconstrained estimation.

The contributions of mitral annular (MA) and leaflet (ML) remodeling to functional mitral regurgitation (FMR) are a key factor in the consideration of mitral valve annuloplasty. Selection of the synthetic ring size and type is based on the quantification of MA and ML remodeling. The MV modeling may be used to quantify MA and ML remodeling in FMR.

From the 4D anatomical model of the MV as constrained by the dynamic system, different metrics may be calculated. The dynamic change of the anterior-posterior (AP) annular diameter, computed as the difference diameter between early systole and early diastole, may discriminate the normal patients from FMR patients. The change in diameter may indicate a reduced accentuation of the saddle shape with consequent reduction in leaflet coaptation. In addition to a dilated, akinetic annulus, the anterior surface length may be larger for patients with FMR. The choice of ring size and type may be based on these automated measurements. Automated 3D quantitative surgical anatomy in FMR shows that an akinetic annulus is an early basis for MR, followed by annular dilatation and anterior leaflet lengthening, and that these mechanistic insights and the quantitative characterization of the pathological anatomy may aid surgical decision-making.

Figure 4:
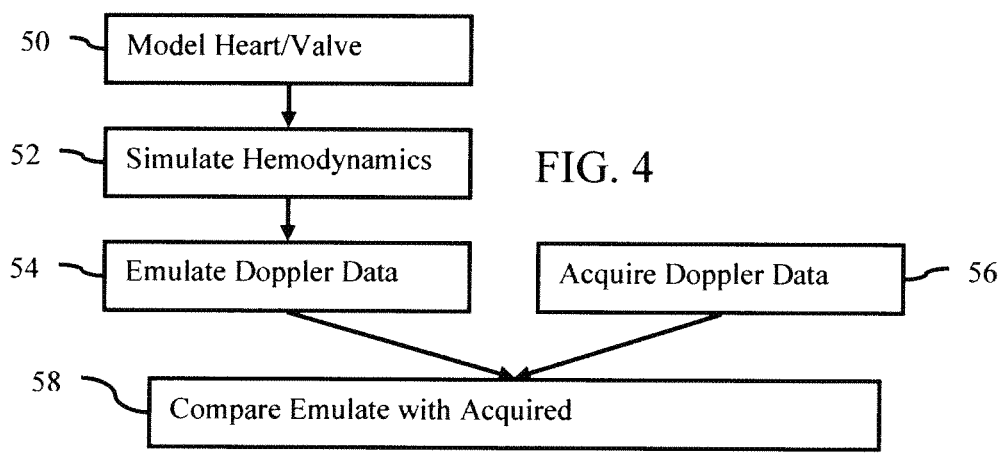
FIG. 4 is a flow chart diagram of one embodiment of a method for validation of hemodynamics in heart modeling.

Referring to FIG. 4, a method for validation of hemodynamic simulation of a heart is shown. The method is implemented by a medical diagnostic imaging system, a review station, a workstation, a computer, a PACS station, a server, combinations thereof, or other device for image processing medical diagnostic data. For example, the system or computer readable media shown in FIG. 9 implements the method, but other systems may be used. The method is implemented in the order shown or a different order. Additional, different, or fewer acts may be performed.

The acts are performed to validate hemodynamics for an estimated model. The acts may be performed automatically by a processor. The user may activate the process. Once activated, the anatomy is modeled, hemodynamics are simulated, and Doppler data is emulated from the hemodynamics. The emulated Doppler data may be compared to actual acquired Doppler data to validate the simulation of the hemodynamics from the estimated model. The validation is performed without further user input. User input of locations of the anatomy in any of the scan data may be avoided. Some user input may be provided, such as for changing modeling parameter values, correcting detected locations, and/or to confirm accuracy of location estimation.

The model is designed for clinical use. Cardiovascular disease management may be supported by accurate, fast and ubiquitous imaging technologies and/or quantification. The clinical decision making process may benefit from validated, automated modeling.

Non-respondent patients are common in cardiac disease, presenting in numerous cases unexpected adverse events because the therapy is not adapted to that specific patient. Patient-specific modeling may limit unexpected adverse events. Therapeutic decisions may be based on patient-specific information instead of or as well as results obtained in population-based studies.

The complex interdependency of anatomy, function and hemodynamics may benefit from systematic analysis of the whole organ (e.g., heart) to accurately assess dysfunction and associated morbidities. The method of FIG. 4 provides for patient-specific models that 1) may provide the cardiologist with accurate, quantitative, and reproducible biomarkers of the cardiac function, 2) may give insights and predict comorbidites within the complex interconnected cardiovascular system, and 3) may predict, beforehand, the outcome of a therapy. These models may support personalized, preventive, and/or predictive healthcare by predicting disease progress and therapeutic outcomes.

Patient-specific modeling may be useful for computational fluid dynamics (CFD). CFD in cardiac models may integrate into a holistic view the organ anatomy, dynamics and hemodynamics. Due to the lack of personalized representations, fluid dynamics equations are often solved on generic models built from at most one cardiac phase with simplified motion. Data-driven patient-specific models of anatomy, dynamics and hemodynamics may be provided.

The model is of the heart or a portion of the heart. For example, a patient-specific model of left-heart anatomy, dynamics and hemodynamics is provided in act 50. Fast and robust patient-specific parameter estimation from four-dimensional transesophageal echocardiography (TEE) or other data is used to estimate surfaces representing the heart. The Navier-Stokes equations may be solved to provide the hemodynamics in act 52. A qualitative and/or quantitative validation against clinical Doppler echocardiography is performed in act 58.

Figure 5:
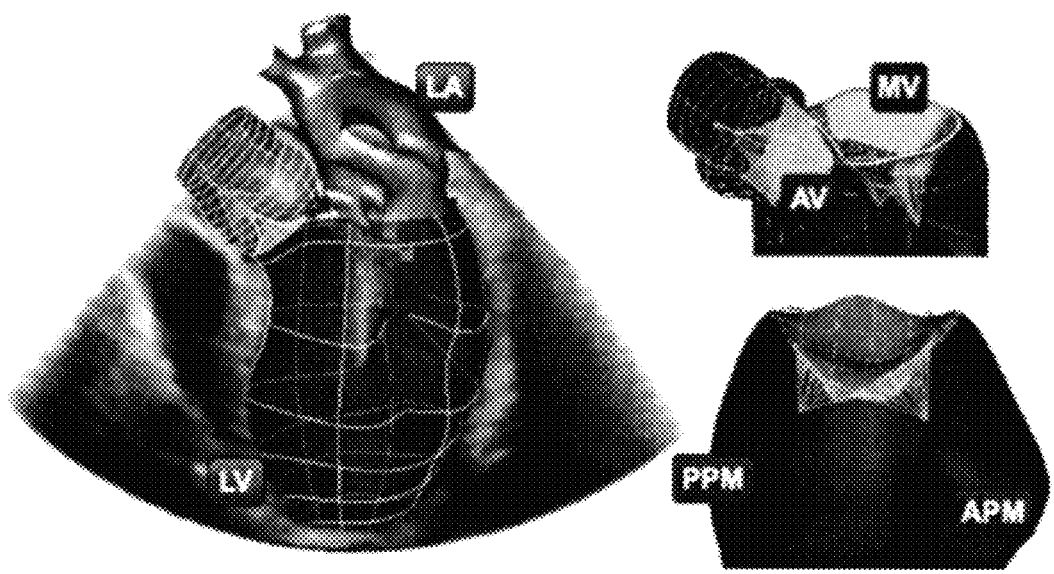
FIG. 5 is an illustration of example landmarks and mesh for a heart.

In act 50, the heart is modeled. The model may be of the entire heart or a portion of the heart. The portion may include one or more valves. The model may be just of the valve, such as the model discussed above for FIG. 1. In one embodiment, a holistic four-dimensional model of the left heart includes the left ventricle (LV), left atrium (LA), aortic valve (AV), mitral valve (MV) and the anterior and posterior papillary muscles (APM and PPM) of the MV. FIG. 5 shows an example of the model and the component parts. The left image of FIG. 5 is the full model of the left heart estimated from TEE data. The top right image is a view of the aortic and mitral valve with volumetric leaflets. The bottom right image is a septal view of the left ventricular papillary muscles. Additional, different, or fewer components may be included in the model.

The same or different model or estimation is performed for each part of the heart. Given the physiological complexity of the left heart, a modular and hierarchical approach may facilitate capturing a broad spectrum of morphological and pathological variations. The model is parameterized. For example, four time dependent similarity transforms for each anatomical structure (LV, LA, AV and MV) include their global location, orientation and scale over the cardiac cycle, denoted by $B(t)_m$, $m \in \{LV, LA, AV, MV\}$. Twenty or other number of trajectories of anatomically defined landmarks $I_n \in R^3$ (e.g., 3 commissures, 3 hinges, 3 tips and 2 ostia for the aortic valve, 3 trigones, 2 commissures, 2 tips and 2 papillary heads for the mitral valve), $L(B, t) = \{I_1, I_2, \ldots, I_{20}\}$ are included. Nine or other number of dense meshes $M_q$ with $K_q$ vertices represent the LA, LV, aortic root, three aortic leaflets, two mitral leaflets and the aortic-mitral continuity $M_q(B, L, t) = \{v_1, v_2, \ldots, v_{Kq}\}$, $v_i \in R^3$ being the position of the $i^{th}$ vertex, which are constrained by the previously defined landmarks, are provided. Other parameterizations may be used.

The patient-specific parameters of the valvular apparatus and left ventricle are estimated from 4D TEE images using a hierarchical discriminative learning algorithm, such as discussed above for FIG. 2 with or without the constraint of the biomechanics. The a posteriori probability $p(B, L, M|I)$ of the model given the image data I is incrementally modeled within the Marginal Space Learning (MSL) framework. The similarity transforms B (e.g., translation, rotation, and/or scaling) and the anatomical landmarks L are estimated automatically by detectors successively trained on the marginal spaces using the Probabilistic Boosting Tree (PBT) with Haar and/or steerable features. The complex local motion of the surface structures is estimated with a combination of the aforementioned techniques and speckle tracking.

The left atrium (LA) and pulmonary veins are commonly only partially visible in TEE acquisitions. The LA fitting may be performed semi-automatically using constraints provided by the mitral annulus and statistical models of shape and motion obtained from a large CT database. The CT information is used to complete the surface of the LV indicated by the ultrasound TEE data. The user may refine this fit.

In one embodiment, valve leaflets are volumetrically modeled by representing them with ventricular and arterial/atrial surfaces (see FIG. 5, top right). A thickness is added to the leaflets, such as 1 mm. The papillary muscles are represented as part of the left ventricular endocardium, constrained by the papillary heads (see FIG. 5, bottom right). Chordae may be added to extend from the papillary heads to the valve. These aspects consider the spatial presence and displacement of blood. The model may include the longitudinal, radial and circumferential left ventricular motion to capture the full momentum exercised by the endocardial wall onto the blood.

The meshes for each component of the heart may be uniquely parameterized through the anatomical landmarks $I_n$. The meshes may be joined together by three-dimensional filtering, warping, or other fitting operations. The temporal point correspondence is implicitly guaranteed by the unique parameterization of the landmarks.

In act 52, the hemodynamics are simulated from the modeling of the heart. Any hemodynamic simulation may be used, such as tracking the surfaces for the heart over time to calculate resulting flow caused by the motion. A measured or estimated blood pressure may be used to simulate the flow.

Any solution for CFD may be used, such as finite element methods. In order to simulate the hemodynamics using a heart model, the CFD solver handles the large deformations of the non-manifold heart surface, including multiple topological changes like valve closure. Such constraints pose difficulties for body-fitted grid methods like the finite element method. To address these difficulties, a level-set-based embedded boundary method may be used. The non-manifold heart polygonal mesh is embedded in a computational box endowed with a regular grid. The grid is three-dimensional. The Navier-Stokes equations are solved inside the rectangular domain using finite difference and finite volume discretizations. The differences between the mesh or heart wall surface and the grid locations are used to solve Navier-Stokes equations. The liquid inside the box and "outside" the left heart plays the role of the body circulatory system, whose flow resistance is simulated by imposing no slip boundary conditions on the sides of the box. The heart polygonal mesh is represented on the regular grid with spatial resolution dx by defining the level set $\phi(x)=\text{dist}(x, \text{mesh})-dx$, and using the mesh appropriately for defining the numerical stencils at the blood/tissue interface.

The 3D Navier-Stokes equations may be solved for incompressible flow with viscous terms. Blood density and dynamic viscosity are set to $\rho_{liquid}=1.05$ g/cm$^3$ and $\mu=0.003$ Pa·s, respectively. The velocity of the mesh walls, extrapolated in space to the grid nodes and interpolated in time between two consecutive mesh positions, are used to enforce no-slip conditions to the Navier-Stokes solver. The ghost fluid method may extend the velocity in the solid regions, when necessary. The convective solver relies on high-order Courant-Isaacson-Rees (CIR) techniques, while the viscous terms are treated semi-implicitly. An efficient multi-grid preconditioned conjugate gradient solver is used to solve the pressure Poisson equation.

Figure 6:
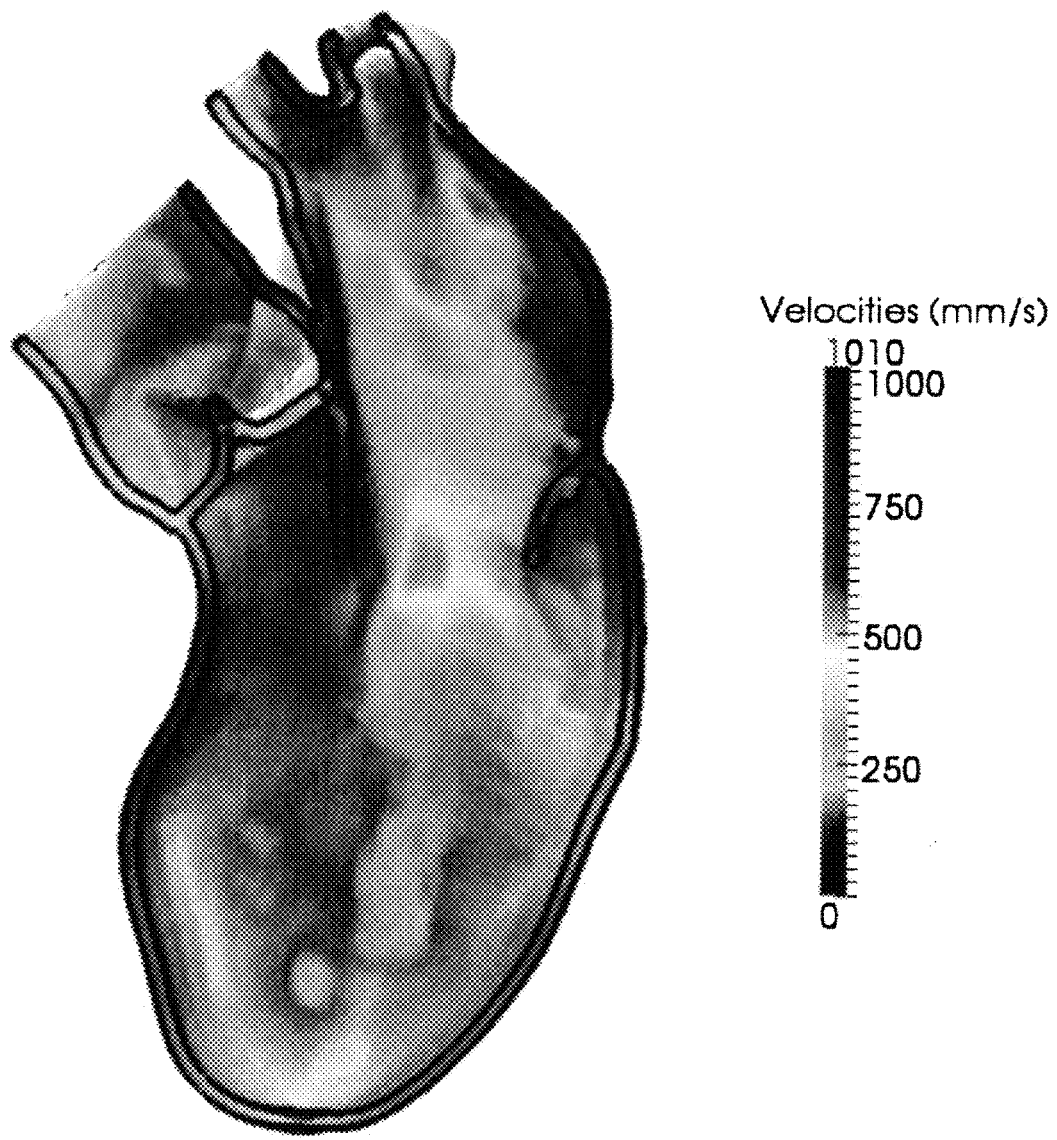
FIG. 6 shows example estimated velocities using simulation from a model, according to one embodiment.

In an example, the simulation computations are performed on grids with an isotropic cell resolution of 1 mm (i.e., dx=1 mm), which is in the same range as the TEE data resolution. The time step obeys the Courant-Friedrichs-Lewy (CFL) condition dt*max(u)<dx, which enforces that information carried by the blood velocity u does not travel faster than one grid cell per time step. The result of the computational fluid dynamics simulation is illustrated for a specific patient in FIG. 6. FIG. 6 is a cross-section of the left portion of the heart in early diastole. While shown as a two-dimensional cross-section, the velocities are determined as three-dimensional velocity vectors.

Referring again to FIG. 4, Doppler data is emulated from the simulated hemodynamics. Ultrasound data is emulated from the velocities determined in act 52.

For validation of simulated heart hemodynamics, the emulated Doppler data may be compared with clinically acquired Doppler measurements in act 58. For the comparison, Doppler data is acquired by scanning the patient in act 56. Doppler echocardiography is routinely performed during cardiac exams to determine blood velocities from the phase shift between emitted and reflected high frequency ultrasound waves. Due to the scanning from the transducer, the ultrasound data represents a measure of velocities along the probe or scan line direction. The velocities are one-dimensional or velocity along the scan line.

Continuous wave (CW) Doppler and/or pulse wave (PW) Doppler are used to measure the velocities. CW returns the velocities of all blood cells along the probe path or scan line. The outer envelope of the signal corresponds to the maximum velocity. CW may be used to acquire the very high speed of regurgitation flows, however, without providing spatial measurement.

PW returns the dominant velocity of the blood cells inside a focal region of interest (ROI). PW may be steered to scan different locations. The Doppler effect from a sequence of transmit beams and corresponding echoes repeated for different scan lines provides velocities for the different locations. The ROI may be a line, area, or volume. The ROI may include all or a portion of the heart. For example, the ROI is positioned below the mitral leaflet tips and/or within the left ventricular outflow tract. PW Doppler is used to measure the blood inflow and/or outflow across the valves and is limited in capturing high velocities.

Figure 7:
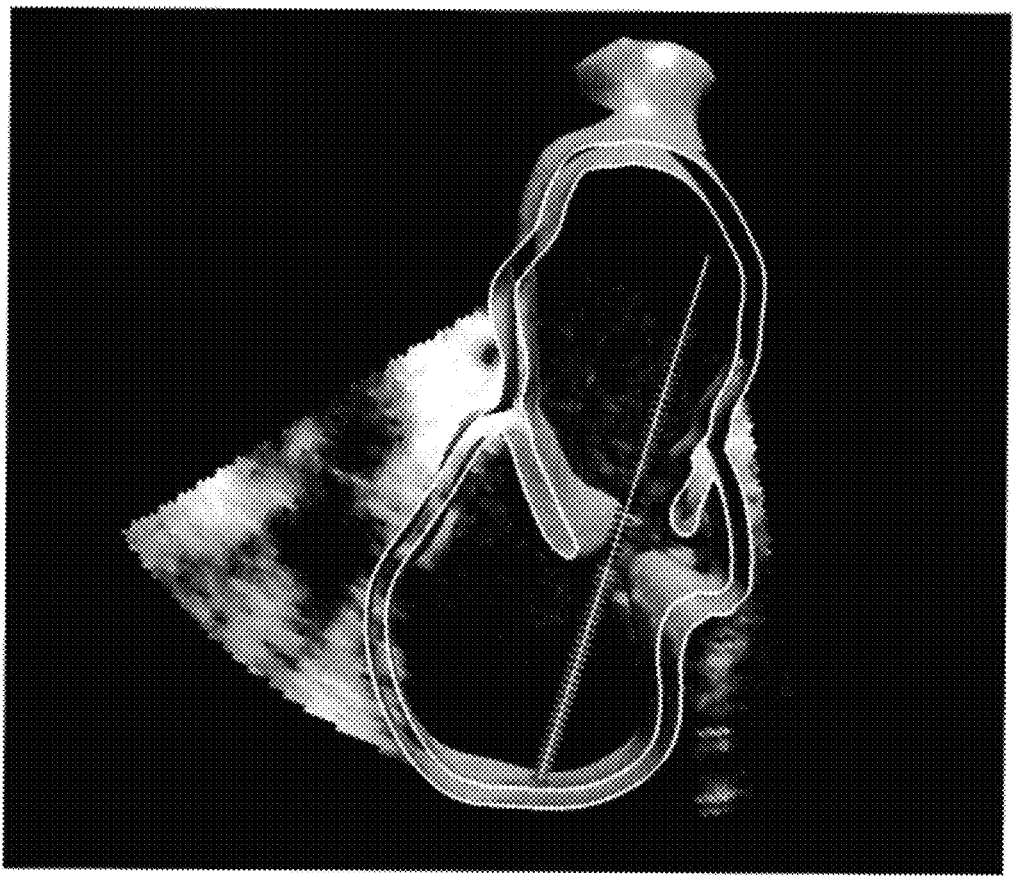
FIG. 7 is an example medical image with a scan line for Doppler imaging placed relative to the heart.

For comparison in act 58, similar one-dimensional signals are reconstructed from the simulated 4D CFD velocities in act 54. In the 4D patient-specific computational model, a virtual CW probe path is defined to match the real position and orientation of the corresponding ground truth Doppler scan line. FIG. 7 shows an example scan line through a cross-section of the heart. The 4D velocities from the simulation are projected onto the probe direction for the entire cardiac cycle. For each cardiac phase, the maximum velocity values along the probe path are identified. Velocities are sampled in 1 mm spatial steps along the probe path and at each location averaged over a small disk of radius 1.5 mm, to realistically match the resolution of the CW protocol.

For the emulation of PW values, virtual PW scan lines and ROI are defined to match the real position and orientation of the corresponding ground truth Doppler acquisition. The 4D simulated velocities inside the ROI are projected along the scan line or scan lines. The lines are parallel (i.e., linear scan pattern) or non-parallel (e.g., sector or Vector® scan pattern). For each sample location, the dominant velocity of the blood cells is approximated by the most frequent velocity found in the ROI, determined automatically using a histogram. In one example, the number of points in the ROI varies between 300 and 700, while 10 bins are used to build the histogram. The ROI does not move over time. The histogram is therefore computed at every time step from the same location. The temporal resolution of the simulation may be higher, yielding more "defined" curves. The process mimics the Doppler acquisition.

The example emulation is of transvalvular blood velocities. Such regions may be routinely measured during Doppler ultrasound exams. Other regions may additionally or alternatively be used.

Figure 8:
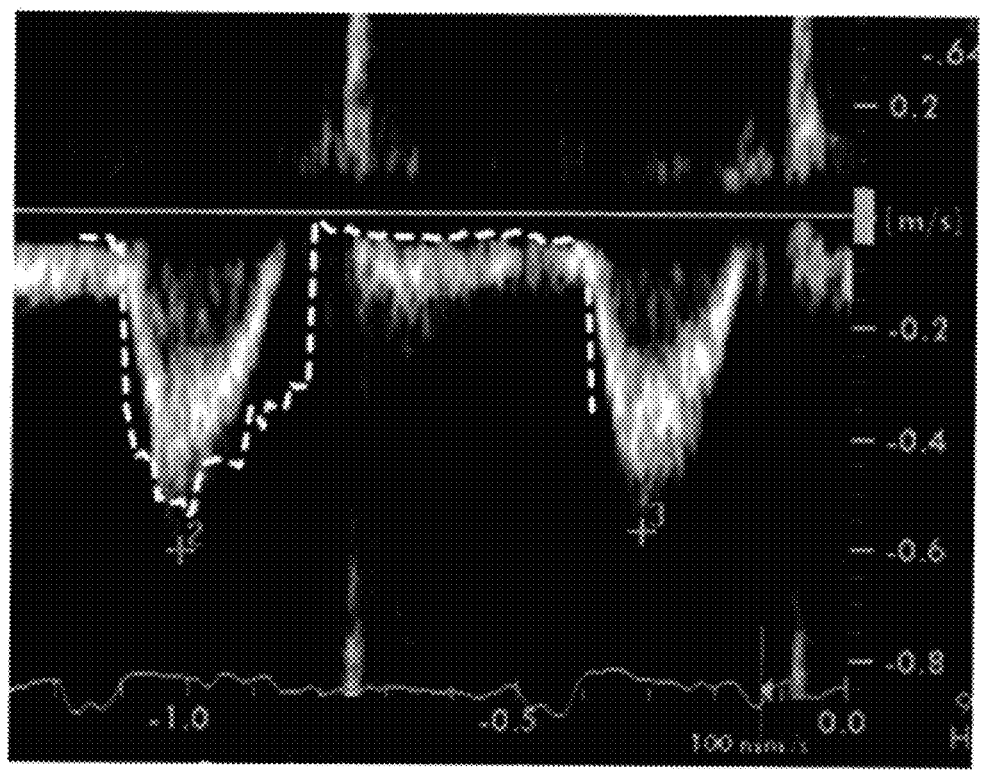
FIG. 8 shows an example of pulsed wave velocity graph based on emulation from a model and as acquired from ultrasound scanning.
Figure 9:
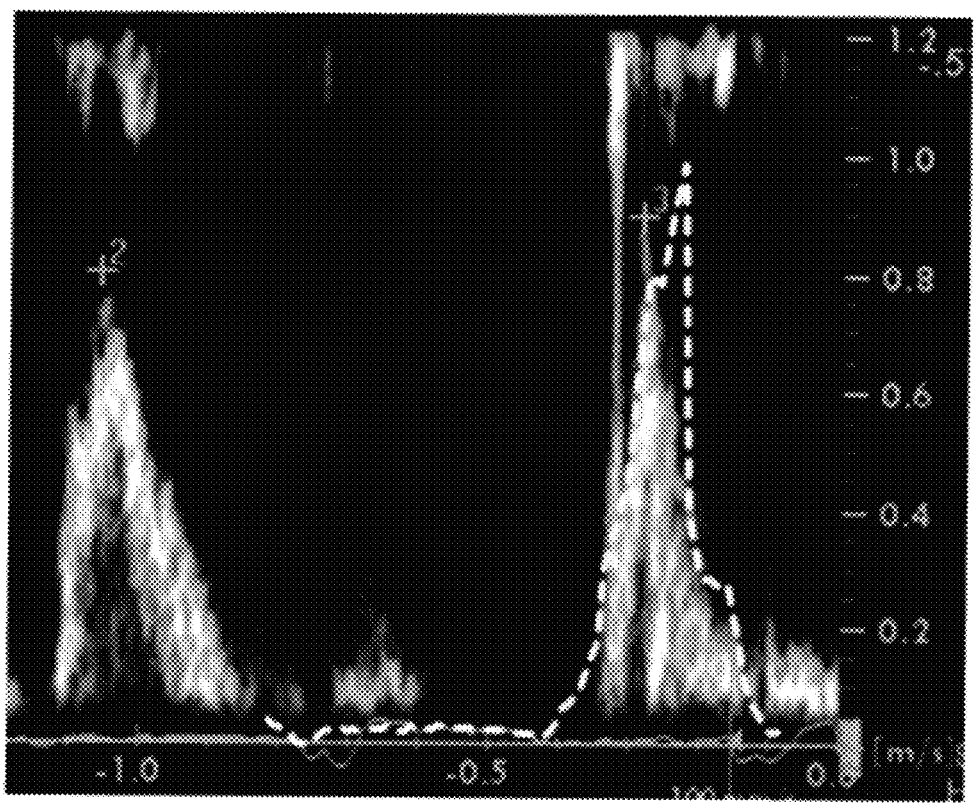
FIG. 9 shows an example of continuous wave velocity graph based on emulation from a model and as acquired from ultrasound scanning.

For the comparison of act 58 in FIG. 4, the acquired Doppler ultrasound data is compared with the emulated Doppler ultrasound data. FIG. 8 shows comparison for PW Doppler. The dashed line represents the maximum velocity over time emulated from the simulation of hemodynamics. The emulation waveform is overlaid with a PW image for comparison. The time period represented in the image is associated with atrial fibrillation. The comparison is visual. FIG. 9 shows comparison for CW Doppler.

The absence of the A-Wave in transmitral measurements may be captured with the example models and hemodynamics discussed above. The high velocity peaks in CW aortic measurements may similarly be captured with the example models and hemodynamics discussed above.

In other embodiments, the comparison is quantified. For example, a difference in velocity is calculated for each time and/or location. The difference is averaged or plotted over time. Other quantifications of the differences may be used. In yet other embodiments, the comparison is not done, and the computed Doppler is used directly The amount of difference may validate the anatomical model and associated hemodynamics. Once validated, the model may be used for clinical evaluation of the heart function. Since the anatomical model relies on patient-specific data, the model and associated hemodynamics may more likely be accurate relative to the given patient rather than generalized. Patient specific validation may be used in some embodiments.

In one example, the performance of the patient-specific anatomy and dynamics computation is validated on a set of 239 patients with 4D echocardiography acquisitions. On average, the precision is 1.73 mm at a speed of 4.8 sec per volume for the valvular model and 2.68 mm at a speed of less than 1 sec per volume for the left ventricle.

The validation of the patient-specific hemodynamics computation is performed against clinically relevant blood flow measurements, routinely acquired using Doppler echocardiography techniques. Doppler methods, such as the aortic CW Doppler for stenosis assessment, are the current gold standard for hemodynamic analysis. The diagnostic value of Doppler measurements is to a large extent in the peak velocities for assessing the degree of dysfunction and/or qualitative observations in particular modes, such as the E- and A-waves in Mitral PW Doppler, describing transmitral flow early and late diastole respectively. Other comparisons for validation may be used.

The model may be validated based on any comparison, such as two patients suffering from atrial fibrillation and a third suffering from severe regurgitations of both aortic and mitral valves. For each patient, a Doppler exam is performed six to 12 weeks before surgery, at the beginning of which 4D TEE data is acquired. A difference in heart rates of 1 to 18% may be observed. Patient-specific models of anatomy and dynamics are computed from the 4D TEE images. From the obtained models, boundary conditions are derived and used to compute patient-specific hemodynamics. Using the validation protocol, measured and computed Doppler (PW and CW) for both valves and all patients are compared. Overall, a high agreement may be observed between the in vivo acquired measurements and computed results and the correlation among the corresponding values, which is computed using all values from all patients, may amount to r=0.85 (significance $\rho<0.0002675$). FIG. 8 represents a qualitative comparison display of the ground truth Doppler velocities over time and the computed curve in one patient with atrial fibrillation. The overlay reveals the high level of detail of the computational model.

The absence of A-wave in the transmitral measurements as specific for atrial fibrillation may be correctly captured by the model. Moreover, sharp peaks observed in CW Doppler across aortic valve are reproduced by the simulation, which occur across the valve orifice just before closure and after opening.

FIG. 9 shows a system for physically-constrained modeling of a heart and/or validation of heart computational models. The system includes a transducer 18, an ultrasound scanner 10, and a display 16. The ultrasound scanner 10 includes a processor 12 and a memory 14. In alternative embodiments, the system is a CT scanner or system. In yet other embodiments, the system is a workstation, computer, or server for simulating using data acquired by a separate system in real-time or using previously acquired patient-specific data stored in a memory. For example, an ultrasound scanner 10 is provided for acquiring ultrasound data representing a volume, and a separate database, server, workstation, and/or computer is provided for creating a model, detecting anatomy, and/or validating the model. Additional, different, or fewer components may be used.

The ultrasound scanner 10 includes a transmit beamformer, receive beamformer, B-mode detector, Doppler detector, harmonic response detector, contrast agent detector, scan converter, filter, combinations thereof, or other now known or later developed medical diagnostic ultrasound system components. As another example, the transducer 18 is not provided, such as where the system is a workstation for off-line or later measurement of valve anatomy.

The transducer 18 is a piezoelectric or capacitive device operable to convert between acoustic and electrical energy. The transducer 18 is an array of elements, such as a multi-dimensional or two-dimensional array. Alternatively, the transducer 18 is a wobbler for mechanical scanning in one dimension and electrical scanning in another dimension. In another embodiment, the array is a one-dimensional array on a cardiac catheter or a TEE probe. Multi-dimensional arrays or a plurality of one-dimensional arrays may be provided on a TEE probe.

The ultrasound scanner 10 uses the transducer 18 to scan a heart volume of a patient. Electrical and/or mechanical steering allows transmission and reception along different scan lines in the volume. Any scan pattern may be used. For example, a plurality of different planes through the heart is scanned by rotating a TEE array, moving a catheter array, or volume scanning with a matrix array. In one embodiment, the transmit beam is wide enough for reception along a plurality of scan lines. In another embodiment, a plane, collimated or diverging transmit waveform is provided for reception along a plurality, large number (e.g., 16-64 receive beams), or all scan lines.

The scan provides the medical diagnostic ultrasound data representing the heart, part of the heart, or valve volume (e.g., mitral valve) at different times as a sequence. The scan is repeated to provide data for the volume at different times. Ultrasound data representing a volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data may be of any type, such as B-mode, flow mode (e.g., PW Doppler), spectral mode (e.g., CW Doppler), Doppler mode, contrast agent, harmonic, or other ultrasound modes of imaging.

The memory 14 is a buffer, cache, RAM, removable media, hard drive, magnetic, optical, database, or other now known or later developed memory. The memory 14 is a single device or group of two or more devices. The memory 14 is shown within the system 10, but may be outside or remote from other components of the system 10.

The memory 14 stores the ultrasound data, such as ultrasound data representing a heart or valve volume at different times in a heart cycle. The heart volume includes at least one valve, but other portions of the heart may be represented. The memory 14 stores flow (e.g., velocity, energy or both), spectral, and/or B-mode ultrasound data. Alternatively, the medical image data is transferred to the processor 12 from another device. The medical image ultrasound data is a three-dimensional data set, or a sequence of such sets. The data represents a three-dimensional region. Any format may be used, such as voxels interpolated to a three-dimensional grid or data representing parallel or non-parallel planes. For CW or PW Doppler, the ultrasound data may represent a volume, an area, a line, or a point.

For real-time imaging, the ultrasound data bypasses the memory 14, is temporarily stored in the memory 14, or is loaded from the memory 14. Real-time imaging may allow delay of a fraction of a second, or even seconds, between acquisition of data and imaging with measurements. For example, real-time imaging is provided by generating the images substantially simultaneously with the acquisition of the data by scanning. While scanning to acquire a next or subsequent set of data, images and measurements are generated for a previous set of data. The imaging occurs during the same imaging session or patient appointment used to acquire the data. The amount of delay between acquisition and imaging for real-time operation may vary, such as a greater delay for initially locating valve anatomies with less delay for measurements. In alternative embodiments, the ultrasound data is stored in the memory 14 from a previous imaging session and used for measuring and/or generating a planar reconstruction without concurrent acquisition.

The memory 14 is additionally or alternatively a non-transitory computer readable storage medium with processing instructions. The memory 14 stores data representing instructions executable by the programmed processor 12 for physically-constrained modeling of a heart or validation of models based on hemodynamics. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multi-processing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The processor 12 is a general processor, digital signal processor, three-dimensional data processor, graphics processing unit, application specific integrated circuit, field programmable gate array, digital circuit, analog circuit, combinations thereof, or other now known or later developed device for processing medical image data. The processor 12 is a single device, a plurality of devices, or a network. For more than one device, parallel or sequential division of processing may be used. Different devices making up the processor 12 may perform different functions, such as an automated anatomy detector and a separate device for performing measurements associated with the detected anatomy. In one embodiment, the processor 12 is a control processor or other processor of a medical diagnostic imaging system, such as a medical diagnostic ultrasound imaging system processor. The processor 12 operates pursuant to stored instructions to perform various acts described herein, such as obtaining data, detecting anatomy, measuring anatomy, and/or controlling imaging.

The processor 12 is configured to detect valve anatomy. The valve operates in response to movement of the heart and includes little active muscle movement. The valve anatomy is detected as a function of application of the medical diagnostic imaging data to a machine-learnt probabilistic model. The valve is represented in the sequence from the medical diagnostic imaging data. The detection occurs during a scan of a patient for feedback while the patient is being scanned or at the medical facility. Detection may occur at other times.

In one embodiment, the processor 12 is configured to detect the valve motion by simultaneously solving for location and motion of a landmark. A spectral trajectory model is applied as a machine-learnt probabilistic model. The landmark location may be estimated without other estimation. In another embodiment, a hierarchal model is used by the processor 12 to estimate global motion assuming a rigid heart valve, then non-linear motion of landmarks of the heart valve, and then a surface of the heart valve.

The processor 12 may perform machine learning and/or applies a machine-learnt algorithm. For example, the processor 12 applies a probabilistic model to detect valve anatomy. The probabilistic model is a machine-learned classifier. Any classifier may be applied, such as a model-based classifier or a learned classifier (e.g., classifier based on machine learning). For learned classifiers, binary or multi-class classifiers may be used, such as Bayesian or neural network classifiers. The classifier is instructions, a matrix, a learned code, or other software and/or hardware for distinguishing between information in a medical image.

The classifier may include a plurality of models or classifiers (e.g., detectors) operable together or independently. For example, different probabilistic models are trained for different anatomy or types of motion. The probabilistic models may be joint or dependent. The location of other anatomies is used to limit or define a search space for a current anatomy and/or as a feature input for classification of another anatomy.

The different classifiers for joint classification, marginal space classification, and/or multiple resolution classification are the same or different types of classifiers. The same or different types of classifiers may be used for the same type of classification, such as different types of classifiers being used for different marginal space classification (e.g., the classifier for global motion is different than the classifier for surface location).

In one embodiment, the probabilistic model is formed from a plurality of probabilistic boosting tree classifiers. Separate training and resulting machine-trained classifiers are provided for each type of motion of interest. For each of these separate classifiers, separate probabilistic boosting tree classifiers are provided for each of the marginal space types. For example, the classifiers follow the marginal space learning protocol.

For application, the processor 12 calculates features for classification. The same or different features are used for classification in each stage. Using a machine-trained translation classifier, the features are used to rule out hypotheses, leaving a subset of remaining hypotheses.

The features are three-dimensional features. 3D data is used to calculate the features. The window function defining the data is a cube, but may have other volume shapes. The window is translated, rotated, and scaled as part of searching for an anatomy. The same or different sized windows are used for different anatomies.

Any features may be used. Different types of features may be used for the same classifier, or all of the features are of a same type for a given classifier. In one embodiment, Haar wavelet-like and/or steerable features are calculated. Haar wavelet-like features represent the difference between different portions of a region. Any number of features may be used, such as tens, hundreds, or thousands. The machine learning process may operate to determine a desired subset or set of features to be used for a given classification task. In one embodiment, the type of features used is gradient features. For example, the "steerable" features are used. Other types of features may alternatively or additionally be used.

The processor 12 is configured to constrain the estimates. The detection of the anatomical locations is based, at least in part, on a constraint from a biomechanical property of the heart. By applying a dynamic system, the anatomy detected for different times may be used to deform the estimation of the locations of the anatomy. The estimation and deforming may be applied iteratively until convergence.

The processor 12 may be configured to generate a representation of the heart or portion of the heart. For example, a display is generated of the valve, left ventricle, or other portion of the heart. The display is of an image for one phase or a sequence of images showing different phases. As another example, a quantity is calculated and output on the image display, as a number or as part of a graph. Any quantity may be calculated from the generated model, such as a quantity representing a characteristic of the valve motion. In one embodiment, the quantity is a function of information for two heart valves.

In one embodiment, the classifier is trained with measurement annotations, such as caliper positions. The detection of the anatomy provides the caliper positions as an output of the classifier. The measurement corresponding to the caliper position is performed, such as measuring a diameter or distance.

The processor 12 may be configured to calculate flow information. Hemodynamics are simulated using a model of the anatomy. Where the model is based on patient-specific information (e.g., imaging data), the resulting hemodynamics (e.g., velocities or other characteristic of flow) represents the flow for that patient. The flow information may be used for imaging or quantification.

The processor 12 may be used to validate the modeling based on the hemodynamics. The 3D or 4D velocity or flow vectors are converted into 1D data representing Doppler data as if acquired by an ultrasound system. The magnitude of the velocity or other flow characteristic along one or more scan lines is determined. This 1D data emulates Doppler data. The processor 12 may compare the acquired Doppler data with the emulated Doppler data for validation. Where the comparison indicates sufficient (e.g., threshold amount) similarity at one or more times and/or regions of interest, the model may be validated for applications associated with the time or region.

The processor 12 generates an image. The anatomy model or hemodynamics model is used to generate an image. The patient-specific scan data may be used for imaging. The image provides a visualization of the heart or valve.

The display 16 is a CRT, LCD, plasma, projector, printer, or other output device for showing an image. The display 16 displays an image of the detected anatomy, such as an image of a valve rendered from medical data and overlaid or highlighted based on the estimates of the valve position. The display 16 displays a sequence of renderings to generate a visualization of the valve motion through the sequence. The visualization may be generated during a same examination session as the scan. The detected anatomy may or may not be segmented, such as just displaying the valve.

A value of a measurement may be displayed. The value may be displayed in a chart, graph, and/or on an image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for physically-constrained imaging a heart, the method comprising:
    acquiring first and second medical diagnostic data representing a patient with a medical scanner;
    estimating, with a processor, first anatomy locations of a valve of the patient from the first medical diagnostic data of the patient at a first time;
    estimating, with the processor, second anatomy locations of the valve of the patient from the second medical diagnostic data of the patient at a second time different than the first time;
    altering the first anatomy locations for the first time as a function of the second anatomy locations and a biomechanical model relating physical mechanics of the valve from the first and second times;
    altering the second anatomy locations for the second time as a function of the first anatomy locations and the biomechanical model; and
    generating an image as a function of the altered first or second anatomy locations.

2. The method of claim 1 wherein estimating the first and second anatomy locations comprises estimating from ultrasound data representing a volume including the valve over time.

3. The method of claim 1 wherein estimating the first and second anatomy locations comprises estimating by application of the first and second medical diagnostic data, respectively, as input features to a machine-learned matrix.

4. The method of claim 1 wherein estimating the first and second anatomy locations comprises estimating as a function of a discriminative probabilistic model.

5. The method of claim 1 wherein estimating the first and second anatomy locations comprises estimating locations for anterior and posterior papillary tips, mitral annulus, and anterior and posterior leaflets at the first and second times and estimating a mesh for the valve at the first and second times.

6. The method of claim 1 wherein altering the first and second anatomical locations comprises solving with the biomechanical model comprising a finite element model.

7. The method of claim 1 wherein altering the first and second anatomical locations comprises applying a force emulating a spring along a normal direction to the first and second anatomical locations and weighted by an amount of altering.

8. The method of claim 1 wherein altering the first and second anatomical locations comprises altering with the biomechanical model comprising a dynamic system having mass, damping, stiffness, displacement, velocity, and acceleration terms.

9. The method of claim 1 further comprising:
repeating the estimating and altering until convergence; and
repeating the estimating, altering and repeating of the estimating and altering for a third time.

10. The method of claim 1 further comprising:
modeling the heart, including the valve;
simulating hemodynamics from the modeling of the heart;
acquiring Doppler ultrasound data from the heart; and
emulating the Doppler ultrasound data from the simulated hemodynamics.

\* \* \* \* \*